United States Patent
Hwu et al.

(10) Patent No.: US 7,585,826 B2
(45) Date of Patent: Sep. 8, 2009

(54) COMPOSITIONS COUNTERACTING PESTICIDES AND MALODORANTS

(75) Inventors: Jih-Ru Hwu, Taipei (TW); Shwu-Chen Tsay, Taipei (TW)

(73) Assignee: Well-Being Biochemical Corp., Taipei (TW)

(*) Notice: Subject to any disclaimer, the term of this patent is extended or adjusted under 35 U.S.C. 154(b) by 0 days.

(21) Appl. No.: 11/726,703

(22) Filed: Mar. 22, 2007

(65) Prior Publication Data

US 2008/0234158 A1  Sep. 25, 2008

(51) Int. Cl.
*A61K 31/28* (2006.01)

(52) U.S. Cl. .............. 510/110; 71/11; 71/26; 71/64.1; 71/903

(58) Field of Classification Search .......... 510/110; 71/26, 11, 64.1, 903
See application file for complete search history.

(56) References Cited

U.S. PATENT DOCUMENTS

| | | | | |
|---|---|---|---|---|
| 4,591,443 A | * | 5/1986 | Brown et al. | 210/747 |
| 5,232,484 A | * | 8/1993 | Pignatello | 558/206 |
| 5,582,627 A | * | 12/1996 | Yamashita | 71/26 |
| 6,336,772 B1 | * | 1/2002 | Yamashita | 405/128.5 |
| 6,569,353 B1 | | 5/2003 | Giletto | |
| 2002/0034421 A1 | | 3/2002 | Kukor | |
| 2004/0234621 A1 | * | 11/2004 | Hwu et al. | 424/617 |
| 2006/0246148 A1 | * | 11/2006 | Hwu et al. | 424/601 |

FOREIGN PATENT DOCUMENTS

| | | |
|---|---|---|
| EP | 1576880 | 9/2005 |
| WO | 91/08049 | 6/1991 |
| WO | 98/16109 | 4/1998 |

* cited by examiner

*Primary Examiner*—Mark Eashoo
*Assistant Examiner*—M. Reza Asdjodi
(74) *Attorney, Agent, or Firm*—Occhiuti Rohlicek & Tsao LLP

(57) ABSTRACT

This invention relates to compositions that counteract chemicals such as pesticides and malodorants. Also disclosed are a method for preparing such compositions and a method for applying such compositions to counteract pesticides or malordorants.

12 Claims, No Drawings

COMPOSITIONS COUNTERACTING PESTICIDES AND MALODORANTS

BACKGROUND

Human beings are increasingly exposed to various hazardous pesticides and malodorants. To minimize such exposure, agents that counteract pesticides and malodorants by chemically modifying them have been used. There is still a need for more effective counteracting agents.

SUMMARY

This invention features a composition useful for counteracting a pesticide or malodorant. The composition includes a catalytic ionic salt and a buffering salt. The catalytic ionic salt contains a cation of Ni, Co, Fe, Cu, Mn, Cr, Ti, Al, Sb, Sn, Pb, Pt, Pd, Os, Ru, Cd, Rh, Ir, or $NH_4$; and an anion of chloride, bromide, iodide, nitrate, sulfate, sulfite, acetate, oxalate, carboxylate, succinate, phosphate, pyrophosphate, perchlorate, gluconate, ascorbate, ethylenediamine tetraacetate, fumarate, or lactate. The buffering salt contains a cation of Li, Na, K, Mg, Ca, or Zn; and an anion of chloride, nitrate, sulfate, carboxylate, hydrogen carbonate, phosphate, dihydrogen phosphate, hydrogen phosphate, oxalate, gluconate, ascorbate, ethylenediamine tetraacetate, or lactate. The weight ratio between the catalytic ionic salt and buffering salt is 1:40-4,000. The composition may further include a third component that is a mixture of a reducing coenzyme and an oxidizing agent, a sulfide, or an ionic compound. The weight ratio between the catalytic ionic salt, buffering salt, and the third component is 1:40-4,000:2-200.

In another aspect, this invention features a method for counteracting a pesticide or malodorant. The method includes applying to a subject an effective amount of the composition described above.

In still another aspect, this invention features a method for preparing a composition useful for counteracting a pesticide or malodorant. The method includes mixing (i) a catalytic ionic salt, (ii) a buffering salt, and (iii) a mixture of a reducing coenzyme and an oxidizing agent, an ionic compound, or a sulfide at the weight ratio of 1:40-4,000:2-200.

The details of one or more embodiments of the invention are set forth in the description below. Other features, objects, and advantages of the invention will be apparent from the description and from the claims.

DETAILED DESCRIPTION

The pesticide or malodorant counteracting composition of this invention includes a catalytic ionic salt and a buffering salt. It may further contain a third component, e.g., a mixture of a reducing coenzyme and an oxidizing agent, an ionic compound, or a sulfide. The weight ratio of the abovementioned three constituents is 1:40-4,000:2-200, and preferably 1:1,200-1,500:10-50. Examples of the catalytic ionic salts include, but are not limited to, nickel chloride, ammonium nickel sulfate, copper chloride, copper sulfate, cuprous chloride, cuprous sulfate, ferric chloride, ferric sulfate, ferrous chloride, ferrous sulfate, manganese chloride, and manganese sulfate. Examples of the buffering salts include, but are not limited to, calcium carbonate, lithium carbonate, magnesium carbonate, potassium carbonate, sodium bicarbonate, potassium bicarbonate, magnesium chloride, sodium chloride, potassium phosphate, potassium hydrogen phosphate, potassium dihydrogen phosphate, calcium sulfate, lithium sulfate, and magnesium sulfate. The reducing coenzyme can be reduced flavin mononucleotide, reduced flavin adenine dinucleotide, reduced nicotinamide adenine dinucleotide, or reduced nicotinamide adenine dinucleotide phosphate; and the oxidizing agent can be hydrogen peroxide or a quinone-based compound. The ionic compound can be that contains a cation of Li, Na, or K and an anion of chloride, bromide, iodide, sulfite, acetate, succinate, pyrophosphate, perchlorate, gluconate, ascorbate, ethylenediamine tetraacetate, fumarate, or lactate. The sulfide can be RSH, in which R is aryl, alkyl, or aralkyl. Alternatively, it can be is cysteine, reduced glutathione, dithiothreitol, or homocysteine.

To prepare a composition of this invention, one can mix the desired components at a predetermined ratio. The components can be added in any order.

The catalytic ionic salt and buffering salt in the composition react with oxygen molecule in the air and activate it to become oxygen free radial anion. The free radical anion then oxidizes a pesticide or malodorant, thereby converting it to a less toxic or stenchful compound. A mixture of a reducing coenzyme and an oxidizing agent, an ionic compound, or a sulfide can also be included in the composition to re-activate the reacted salts so that the salts are recycled.

Examples of chemicals that can be decomposed by the above-described compositions include, but are not limited to, health hazardous pesticides and malodorants, including smoke constituents, shown below:

A. Pesticides
  i) Organophosphorous Pesticides

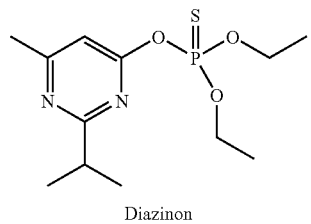

Diazinon

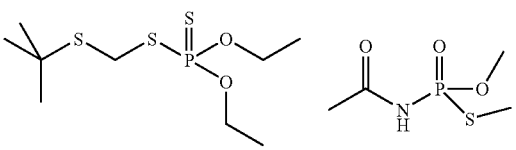

Terbufos                    Acephate

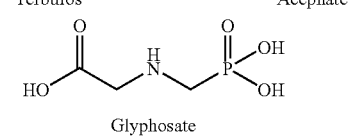

Glyphosate

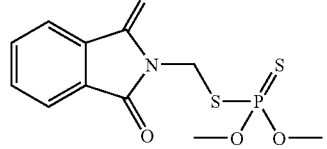

Phosmet

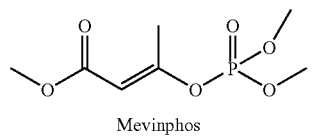

Mevinphos ii) Organonitrogen/Heterocyclic Pesticides
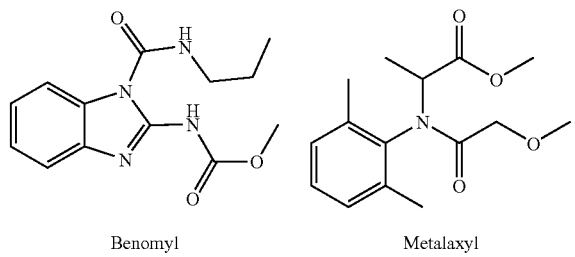
Benomyl            Metalaxyl
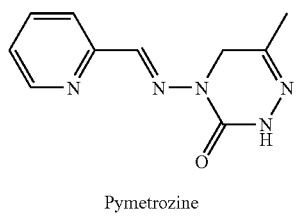
Pymetrozine
iii) Carbamate Pesticides
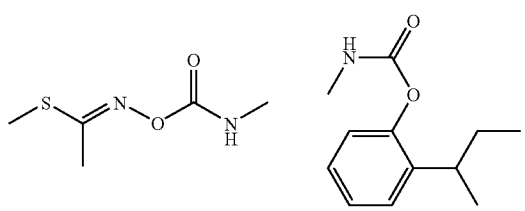
Methomyl            Fenobucard
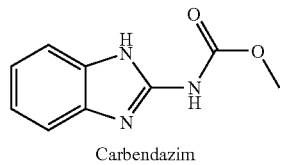
Carbendazim
iv) Urea-Type Pesticide
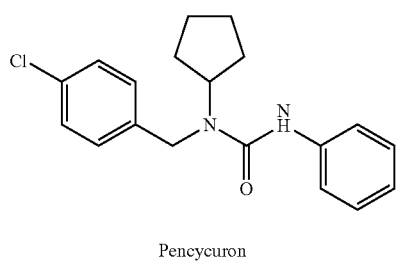
Pencycuron
v) Triazole Pesticide
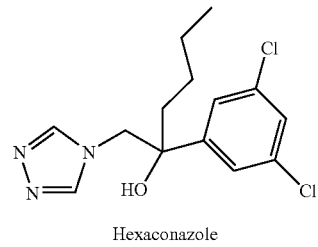
Hexaconazole
vi) Dithiocarbamate Pesticides
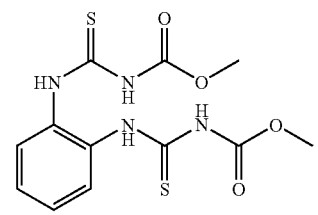
Thiophanate-methyl
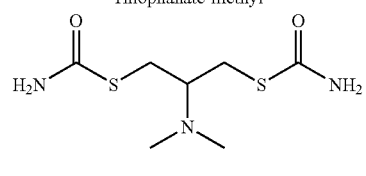
Cartap
vii) Other Pesticides
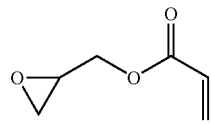
Thiabendazole
B. Malodorants
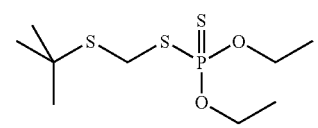
Terbufos
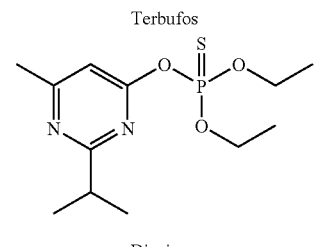
Diazinon -continued

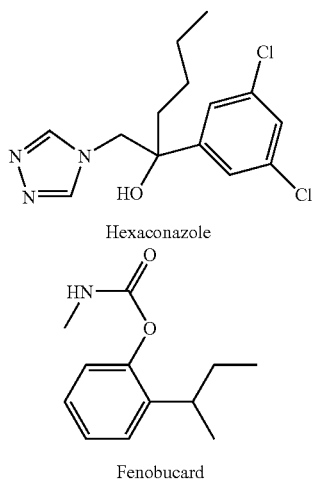

Hexaconazole

Fenobucard

C. Smoke Constituents:

i) Cigarette Smoke Constituent

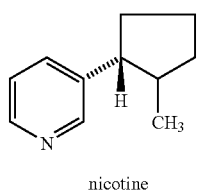

nicotine ii) Barbecue Smoke Constituents

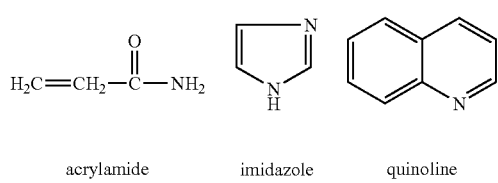

acrylamide    imidazole    quinoline iii) Kitchen Smoke Constituents

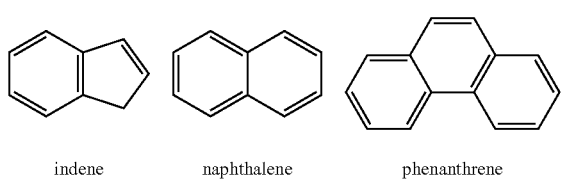

indene    naphthalene    phenanthrene

A composition of this invention can be used to counteract pesticides adhered to crops or fruits. It can also be used to eliminate underarm odor, perspiration odor, sole odor, bad breath, hair odor, or menstrual odor. Further, it can be used to clean contaminated clothes, respirators, masks, gloves, protective equipments, and medical devices. The active time of the composition ranges from 1-100 hours, depending on the concentration and dosage.

The composition can be applied by various methods to a human being or to an object contaminated with a pesticide or malodorant. For example, an aerosol spray can be used to spray the composition onto the target area. As another example, a washing solution containing the composition can be used to immerse a contaminated object. When an aerosol solution is used, it is preferred to have a concentration of $10^{-4} \sim 10^{-6}$ wt %. When a washing solution is used, it is preferred to have a concentration of $10^{-1} \sim 10^{-4}$ wt %.

The six examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLE 1

0.50 g of ammonium nickel sulfate was added to 500 mL of Reverse Osmosis (R.O.) water. The solution was stirred for 15 min at ambient temperature to afford clear solution (A).

15 g of sodium hydrogen phosphate and 15 g of sodium dihydrogen phosphate were added to 9.0 L of R.O. water. The mixture was thoroughly stirred. 120 g of sodium chloride, 40 g of potassium hydrogen carbonate, 5.0 g of calcium sulfate, and 5.0 g of magnesium chloride were sequentially added. The resulting mixture was stirred for 60 min at ambient temperature to give clear solution (B).

10 mL of 3.0% hydrogen peroxide was diluted with 500 mL of R.O. water. To this was added 5.0 g of 1,4-benzoquinone. The solution was stirred for 30 min at ambient temperature. 2.0 g of coenzyme NADPH was added. The resulting solution was stirred for 20 min.

Combined solutions (A) and (C) were stirred for 15 min at ambient temperature. To this was added solution (B). The mixture was thoroughly stirred to provide the desired composition.

EXAMPLE 2

0.50 g of ammonium nickel sulfate was added to 500 mL of R.O. water. The solution was stirred for 15 min at ambient temperature to afford clear solution (A).

15 g of sodium hydrogen phosphate and 15 g of sodium dihydrogen phosphate were added to 9.0 L of R.O. water. The mixture was thoroughly stirred. 120 g of sodium chloride, 40 g of potassium hydrogen carbonate, 5.0 g of calcium sulfate, and 5.0 g of magnesium chloride were sequentially added. The resulting mixture was stirred for 60 min at ambient temperature to give clear solution (B).

50 g of sodium lactate was added into 500 mL of R.O. water. The mixture was stirred for 30 min at ambient temperature to provide clear solution (C).

Solution (A) was added to solution (C), and the mixture was stirred for 15 min at ambient temperature. Solution (B) was then added. The resulting mixture was stirred for 20 min to obtain a composition of this invention.

EXAMPLE 3

0.50 g of ammonium nickel sulfate was added to 500 mL of R.O. water. The solution was stirred for 15 min at ambient temperature to afford clear solution (A).

15 g of sodium hydrogen phosphate and 15 g of sodium dihydrogen phosphate were added to 9.0 L of R.O. water. The mixture was thoroughly stirred. 120 g of sodium chloride, 40 g of potassium hydrogen carbonate, and 5.0 g of calcium sulfate were sequentially added. The resulting mixture was stirred for 60 min at ambient temperature to give clear solution (B).

50 g of cysteine was added into 500 mL of R.O. water. The mixture was stirred for 30 min at ambient temperature to provide clear solution (C).

Solution (A) was added to solution (C), and the mixture was stirred for 15 min at ambient temperature. Solution (B) was then added. The resulting mixture was stirred for 20 min to obtain a composition of this invention.

EXAMPLE 4

The above-prepared composition was tested to decompose 17 pesticides, i.e., Diazinon, Terbufos, Acephate, Glyphosate, Phosmet, Mevinphos, Benomyl, Metalaxyl, Pymetrozine, Methomyl, Fenobucard, Carbendazim, Pencycuron, Hexaconazole, Thiophanate-methyl, Cartap, and Thiabendazole. The decomposition rates were measured as follows:

Each pesticide was dissolved in tap water at a concentration of 10 ppm. 10 mL pesticide solution was mixed with 10 mL of the composition prepared in Example 1 for 5 min. 10 mL pesticide solution was also mixed with 10 mL tap water or 10 mL 10% brine solution to prepare control solution. The pesticide concentration of each tested reaction solution was measured by high performance liquid chromatography.

It showed that in the presence of the composition prepared in Example 1, the pesticide decomposition rate was 2,300~14,000 times higher than that when tap water was used. Also, when the composition of this invention was used, the pesticide decomposition rate was 1,900~11,000 times higher than that when 10% brine solution was used. Among these seventeen pesticides, Terbufos, Acephate, and Hexaconazole were decomposed at higher rates than the others.

EXAMPLE 5

7.5 mL of a pesticide solution, containing 10 ppm Terbufos, Diazinon, Hexaconazole, or Fenobucard, was allowed to react with 2.5 mL of the composition prepared in Example 1 for 1.0 min, 3.0 min, and 5.0 min, respectively. HPLC was used to determine the concentrations of the pesticide.

All of Terbufos, Diazinon, Hexaconazole, and Fenobucard decomposed within 1.0 min, 3.0 min, and 5.0 min, respectively. After 5.0 min of the reaction time, 91% Terbufos decomposed, 87% Diazinon decomposed, 85% Hexaconazole decomposed, and 76% Fenobucard decomposed.

EXAMPLE 6

Seven smoke constituents, i.e., nicotine, acrylamide, imidazole, quinoline, indene, naphthalene, and phenanthrene, were tested for their decomposition in the presence of the composition prepared in Example 1.

9.9 mL of 100 ppm aqueous solution of a smoke constituent was allowed to react for 3.0 min with 0.10 mL of the 20× and 100× compositions, respectively. Gas chromatography was used to determine the concentrations of the remaining smoke constituents. It showed that more than 90% of smoke constituents decomposed after treated with either of the 20× and 100× compositions.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims

What is claimed is:

1. A method for counteracting a pesticide, comprising applying to a subject in need thereof an effective amount of a composition containing a catalytic ionic salt, which contains a cation of Ni, Go, Fe, Cu, Mn, Cr, Ti, Al, Sb, Sn, Pb, Pt, Pd, Os, Ru, Cd, Rh, Ir, or $NH_4$; and an anion of chloride, bromide, iodide, nitrate, sulfate, sulfite, acetate, oxalate, carboxylate, succinate, phosphate, pyrophosphate, perchlorate, gluconate, ascorbate, ethylenediamine tetraacetate, fumarate, or lactate; and a buffering salt, which contains a cation of Li, Na, K, Mg, Ca, or Zn; and an anion of chloride, nitrate, sulfate, carboxylate, hydrogen carbonate, phosphate, dihydrogen phosphate, hydrogen phosphate, oxalate, gluconate, ascorbate, ethylenediamine tetraacetate, or lactate;

wherein the weight ratio between the catalytic ionic salt and buffering salt is 1: 40-4,000, and the subject is a crop, a fruit, a human body, or an article.

2. The method of claim 1, wherein the catalytic ionic salt is nickel chloride, ammonium nickel sulfate, copper chloride, copper sulfate, cuprous chloride, cuprous sulfate, ferric chloride, ferric sulfate, ferrous chloride, ferrous sulfate, manganese chloride, or manganese sulfate; and the buffering salt is calcium carbonate, lithium carbonate, magnesium carbonate, potassium carbonate, sodium bicarbonate, potassium bicarbonate, magnesium chloride, sodium chloride, potassium phosphate, potassium hydrogen phosphate, potassium dihydrogen phosphate, calcium sulfate, lithium sulfate, or magnesium sulfate.

3. The method of claim 1, wherein the composition further contains a mixture of a reducing coenzyme and an oxidizing agent, the weight ratio between the catalytic ionic salt, the buffering salt, and the mixture being 1:40-4,000:2-200.

4. The method of claim 3, wherein the weight ratio between the catalytic ionic salt, the buffering salt, and the mixture is 1:1,200-1,500:10-50.

5. The method of claim 4, wherein the catalytic ionic salt is nickel chloride, ammonium nickel sulfate, copper chloride, copper sulfate, cuprous chloride, cuprous sulfate, ferric chloride, ferric sulfate, ferrous chloride, ferrous sulfate, manganese chloride, or manganese sulfate; the buffering salt is calcium carbonate, lithium carbonate, magnesium carbonate, potassium carbonate, sodium bicarbonate, potassium bicarbonate, magnesium chloride, sodium chloride, potassium phosphate, potassium hydrogen phosphate, potassium dihydrogen phosphate, calcium sulfate, lithium sulfate, or magnesium sulfate; the reducing coenzyme is reduced nicotinamide adenine dinucleotide or reduced nicotinamide adenine dinucleotide phosphate; and the oxidizing agent is hydrogen peroxide.

6. The method of claim 1, wherein the composition further contains a sulfide, in which the weight ratio between the catalytic ionic salt, the buffering salt, and the sulfide is 1:40-4,000:2-200.

7. The method of claim 6, wherein the weight ratio between the catalytic ionic salt, the buffering salt, and the sulfide is 1:1,200-1,500:10-50.

8. The method of claim 7, wherein the catalytic ionic salt is nickel chloride, ammonium nickel sulfate, copper chloride, copper sulfate, cuprous chloride, cuprous sulfate, ferric chloride, ferric sulfate, ferrous chloride, ferrous sulfate, manganese chloride, or manganese sulfate; the buffering salt is calcium carbonate, lithium carbonate, magnesium carbonate, potassium carbonate, sodium bicarbonate, potassium bicarbonate, magnesium chloride, sodium chloride, potassium phosphate, potassium hydrogen phosphate, potassium dihydrogen phosphate, calcium sulfate, lithium sulfate, or magnesium sulfate; and the sulfide is cysteine, reduced glutathione, dithiothreitol, or homocysteine.

9. The method of claim 1, wherein the composition further contains an ionic compound which contains a cation of Li, Na, or K and an anion of chloride, bromide, iodide, sulfite, acetate, succinate, pyrophosphate, perchlorate, gluconate, ascorbate, ethylenediamine tetraacetate, fumarate, or lactate; in which the catalytic ionic salt, the buffering salt, and the ionic compound are different from each other and the weight ratio between the catalytic ionic salt, the buffering salt, and the ionic compound is 1:40-4,000:2-200.

10. The method of claim 9, wherein the weight ratio between the catalytic ionic salt, the buffering salt, and the ionic compound is 1:1,200-1,500:10-50.

11. The method of claim 10, wherein the catalytic ionic salt is nickel chloride, ammonium nickel sulfate, copper chloride, copper sulfate, cuprous chloride, cuprous sulfate, ferric chloride, ferric sulfate, ferrous chloride, ferrous sulfate, manganese chloride, or manganese sulfate; the buffering salt is calcium carbonate, lithium carbonate, magnesium carbonate, potassium carbonate, sodium bicarbonate, potassium bicarbonate, magnesium chloride, sodium chloride, potassium phosphate, potassium hydrogen phosphate, potassium dihydrogen phosphate, calcium sulfate, lithium sulfate, or magnesium sulfate; and the ionic compound is ethylenediaminetetraacetic acid dilithium salt, ethylenediaminetetraacetic acid dipotassium salt, ethylenediaminetetraacetic acid disodium salt, lithium ascorbate, lithium lactate, potassium ascorbate, potassium lactate, sodium ascorbate, or sodium lactate.

12. The method of claim 1, wherein the article is clothes, a respirator, a mask, a glove, a protective equipment, or a medical device.

* * * * *